US012583893B2

(12) United States Patent
Mangoni et al.

(10) Patent No.: US 12,583,893 B2
(45) Date of Patent: Mar. 24, 2026

(54) USE OF ESCULENTIN AND ITS DERIVATIVES FOR USE IN THE TREATMENT OF CYSTIC FIBROSIS

(71) Applicants:UNIVERSITÀ DEGLI STUDI DI ROMA LA SAPIENZA, Rome (IT); FONDAZIONE PER LA RICERCA SULLA FIBROSI CISTICA, Verona (IT); ISTITUTO GIANNINA GASLINI, Genoa (IT)

(72) Inventors: Maria Luisa Mangoni, Rome (IT); Loretta Ferrera, Genoa (IT)

(73) Assignees: UNIVERSITÀ DEGLI STUDI DI ROMA LA SAPIENZA, Rome (IT); Fondazione Per La Ricerca Sulla Fibrosi Cistica, Verona (IT); Istituto Giannina Gaslini, Genoa (IT)

( * ) Notice: Subject to any disclaimer, the term of this patent is extended or adjusted under 35 U.S.C. 154(b) by 908 days.

(21) Appl. No.: 17/768,636

(22) PCT Filed: Oct. 9, 2020

(86) PCT No.: PCT/EP2020/078394
§ 371 (c)(1),
(2) Date: Apr. 13, 2022

(87) PCT Pub. No.: WO2021/074025
PCT Pub. Date: Apr. 22, 2021

(65) Prior Publication Data
US 2024/0109944 A1     Apr. 4, 2024

(30) Foreign Application Priority Data
Oct. 16, 2019     (IT) ........................ 102019000018938

(51) Int. Cl.
*C07K 14/46*          (2006.01)
*A61K 45/06*          (2006.01)
*A61P 11/00*          (2006.01)

(52) U.S. Cl.
CPC ............ *C07K 14/463* (2013.01); *A61K 45/06* (2013.01); *A61P 11/00* (2018.01)

(58) Field of Classification Search
None
See application file for complete search history.

(56) References Cited

PUBLICATIONS

Di Grazia et al. "The Frog Skin-Derived Antimicrobial Peptide Esculentin-1a(1-21)NH2 Promotes the Migration of Human HaCaT Keratinocytes in an EGF Receptor-Dependent Manner: A Novel Promoter of Human Skin Wound Healing?" PLoS One 10: e0128663 (Year: 2015).*
Cappiello et al. "Esculentin-1a-Derived Peptides Promote Clearance of Psuedomonas aeruginosa Internalized in Bronchial Cells of Cystic Fibrosis Patients and Lung Cell Migration: Biochemical Properties and a Plausible Mode of Action" Antimicrobial Agents and Chemotherapy 60:7252-7262. (Year: 2016).*
Cappiello F "Effects of two L-to D-amino acid substitutions on the structural and functional properties of the antimicrobial peptide esculentin-1a(1-21)" Doctoral Thesis, Sapienza Universita Di Roma. (Year: 2017).*
Payne et al. "Activity of innate antimicrobial peptides and ivacaftor against clinical cystic fibrosis respiratory pathogens" International Journal of Antimicrobial Agents 50:427-435. (Year: 2017).*
Chen et al. "In vivo therapeutic efficacy of frog skin-derived peptides against Pseudomonas aeruginosa-induced pulmonary infection" Scientific Reports 7:8548. (Year: 2017).*
"The Proceedings of the 16th Italian Convention of Investigators in Cystic Fibrosis", Multidisciplinary Respiratory Medicine, Biomed Central Ltd, London, UK,vol. 14, No. 1, Feb. 6, 2019 (Feb. 6, 2019), p. 11-12.
Floriana Cappiello et al, "Esculentin-1a-derived peptides promote clearance of P. aeruginosa internalized in cystic fibrosis bronchial cells as well as lung cells migration: Biochemical properties and a plausible mode of action", Antimicrobial Agents and Chemotherapy,Sep. 26, 2016 (Sep. 26, 2016).
Di Grazia Antonio et al, "d-Amino acids incorporation in the frog skin-derived peptide esculentin-1a(1-21)NH2is beneficial for its multiple functions", Jul. 11, 2015 (Jul. 11, 2015), vol. 47, No. 12, p. 2505-2519.

* cited by examiner

Primary Examiner — Sudhakar Katakam
Assistant Examiner — Zachary J Miknis
(74) Attorney, Agent, or Firm — Gregory P. Einhorn; Greer, Burns & Crain, Ltd.

(57)     ABSTRACT

Are disclosed pharmaceutical compositions comprising as active ingredients Esculentin-1a(1-21)NH$_2$ and/or Esculentin diastereomer Esc(1-21)-1c for use for restoring dysregulation of water and/or ions content and/or composition of the periciliary liquid due to mutations of the CFTR gene encoding for Cystic fibrosis transmembrane conductance regulator (CFTR) and for use for the treatment of cystic fibrosis.

6 Claims, 7 Drawing Sheets

Specification includes a Sequence Listing.

A

B

SEQUENCE LISTING

```
<160> NUMBER OF SEQ ID NOS: 11

<210> SEQ ID NO 1
<211> LENGTH: 46
<212> TYPE: PRT
<213> ORGANISM: Rana esculenta

<400> SEQUENCE: 1

Gly Ile Phe Ser Lys Leu Ala Gly Lys Lys Ile Lys Asn Leu Leu Ile
1               5                   10                  15

Ser Gly Leu Lys Asn Val Gly Lys Glu Val Gly Met Asp Val Val Arg
            20                  25                  30

Thr Gly Ile Asp Ile Ala Gly Cys Lys Ile Lys Gly Glu Cys
        35                  40                  45

<210> SEQ ID NO 2
<211> LENGTH: 21
<212> TYPE: PRT
<213> ORGANISM: Artificial Sequence
<220> FEATURE:
<223> OTHER INFORMATION: Synthetic: Esc(1-21)
<220> FEATURE:
<221> NAME/KEY: MOD_RES
<222> LOCATION: (21)..(21)
<223> OTHER INFORMATION: 3' -NH2

<400> SEQUENCE: 2

Gly Ile Phe Ser Lys Leu Ala Gly Lys Lys Ile Lys Asn Leu Leu Ile
1               5                   10                  15

Ser Gly Leu Lys Gly
            20

<210> SEQ ID NO 3
<211> LENGTH: 21
<212> TYPE: PRT
<213> ORGANISM: Artificial Sequence
<220> FEATURE:
<223> OTHER INFORMATION: Synthetic: Esc(1-21)-1c
<220> FEATURE:
<221> NAME/KEY: MOD_RES
<222> LOCATION: (14)..(14)
<223> OTHER INFORMATION: dLeu
<220> FEATURE:
<221> NAME/KEY: MOD_RES
<222> LOCATION: (17)..(17)
<223> OTHER INFORMATION: dSer
<220> FEATURE:
<221> NAME/KEY: MOD_RES
<222> LOCATION: (21)..(21)
<223> OTHER INFORMATION: 3' -NH2

<400> SEQUENCE: 3

Gly Ile Phe Ser Lys Leu Ala Gly Lys Lys Ile Lys Asn Leu Leu Ile
1               5                   10                  15

Ser Gly Leu Lys Gly
            20

<210> SEQ ID NO 4
```

-continued

```
<211> LENGTH: 21
<212> TYPE: PRT
<213> ORGANISM: Artificial Sequence
<220> FEATURE:
<223> OTHER INFORMATION: Synthetic: Esc 2
<220> FEATURE:
<221> NAME/KEY: MOD_RES
<222> LOCATION: (14)..(14)
<223> OTHER INFORMATION: dLeu
<220> FEATURE:
<221> NAME/KEY: MOD_RES
<222> LOCATION: (17)..(17)
<223> OTHER INFORMATION: dphosphoSer
<220> FEATURE:
<221> NAME/KEY: MOD_RES
<222> LOCATION: (21)..(21)
<223> OTHER INFORMATION: 3' -NH2

<400> SEQUENCE: 4

Gly Ile Phe Ser Lys Leu Ala Gly Lys Lys Ile Lys Asn Leu Leu Ile
1               5                   10                  15

Ser Gly Leu Lys Gly
            20

<210> SEQ ID NO 5
<211> LENGTH: 21
<212> TYPE: PRT
<213> ORGANISM: Artificial Sequence
<220> FEATURE:
<223> OTHER INFORMATION: Synthetic: Esc 3
<220> FEATURE:
<221> NAME/KEY: MOD_RES
<222> LOCATION: (14)..(14)
<223> OTHER INFORMATION: dLeu
<220> FEATURE:
<221> NAME/KEY: MOD_RES
<222> LOCATION: (21)..(21)
<223> OTHER INFORMATION: 3' -NH2

<400> SEQUENCE: 5

Gly Ile Phe Ser Lys Leu Ala Gly Lys Lys Ile Lys Asn Leu Leu Ile
1               5                   10                  15

Ala Gly Leu Lys Gly
            20

<210> SEQ ID NO 6
<211> LENGTH: 21
<212> TYPE: PRT
<213> ORGANISM: Artificial Sequence
<220> FEATURE:
<223> OTHER INFORMATION: Synthetic: Esc 5
<220> FEATURE:
<221> NAME/KEY: MOD_RES
<222> LOCATION: (14)..(14)
<223> OTHER INFORMATION: dLeu
<220> FEATURE:
<221> NAME/KEY: MOD_RES
<222> LOCATION: (17)..(17)
<223> OTHER INFORMATION: dAla
<220> FEATURE:
<221> NAME/KEY: MOD_RES
<222> LOCATION: (21)..(21)
<223> OTHER INFORMATION: 3' -NH2

<400> SEQUENCE: 6

Gly Ile Phe Ser Lys Leu Ala Gly Lys Lys Ile Lys Asn Leu Leu Ile
1               5                   10                  15

Ala Gly Leu Lys Gly
            20
```

```
<210> SEQ ID NO 7
<211> LENGTH: 21
<212> TYPE: PRT
<213> ORGANISM: Artificial Sequence
<220> FEATURE:
<223> OTHER INFORMATION: Synthetic: Esc 6
<220> FEATURE:
<221> NAME/KEY: MOD_RES
<222> LOCATION: (14)..(14)
<223> OTHER INFORMATION: dLeu
<220> FEATURE:
<221> NAME/KEY: MOD_RES
<222> LOCATION: (21)..(21)
<223> OTHER INFORMATION: 3' -NH2

<400> SEQUENCE: 7

Gly Ile Phe Ser Lys Leu Ala Gly Lys Lys Ile Lys Asn Leu Leu Ile
1               5                   10                  15

Gly Gly Leu Lys Gly
            20

<210> SEQ ID NO 8
<211> LENGTH: 21
<212> TYPE: PRT
<213> ORGANISM: Artificial Sequence
<220> FEATURE:
<223> OTHER INFORMATION: Synthetic: Esc 7
<220> FEATURE:
<221> NAME/KEY: MOD_RES
<222> LOCATION: (14)..(14)
<223> OTHER INFORMATION: dLeu
<220> FEATURE:
<221> NAME/KEY: MOD_RES
<222> LOCATION: (17)..(17)
<223> OTHER INFORMATION: dThr
<220> FEATURE:
<221> NAME/KEY: MOD_RES
<222> LOCATION: (21)..(21)
<223> OTHER INFORMATION: 3' -NH2

<400> SEQUENCE: 8

Gly Ile Phe Ser Lys Leu Ala Gly Lys Lys Ile Lys Asn Leu Leu Ile
1               5                   10                  15

Thr Gly Leu Lys Gly
            20

<210> SEQ ID NO 9
<211> LENGTH: 21
<212> TYPE: PRT
<213> ORGANISM: Artificial Sequence
<220> FEATURE:
<223> OTHER INFORMATION: Synthetic: Esc 8
<220> FEATURE:
<221> NAME/KEY: MOD_RES
<222> LOCATION: (14)..(14)
<223> OTHER INFORMATION: dLeu
<220> FEATURE:
<221> NAME/KEY: MOD_RES
<222> LOCATION: (21)..(21)
<223> OTHER INFORMATION: 3' -NH2

<400> SEQUENCE: 9

Gly Ile Phe Ser Lys Leu Ala Gly Lys Lys Ile Lys Asn Leu Leu Ile
1               5                   10                  15

Thr Gly Leu Lys Gly
            20

<210> SEQ ID NO 10
<211> LENGTH: 21
<212> TYPE: PRT
```

-continued

```
<213> ORGANISM: Artificial Sequence
<220> FEATURE:
<223> OTHER INFORMATION: Synthetic: Esc 9
<220> FEATURE:
<221> NAME/KEY: MOD_RES
<222> LOCATION: (14)..(14)
<223> OTHER INFORMATION: dLeu
<220> FEATURE:
<221> NAME/KEY: MOD_RES
<222> LOCATION: (17)..(17)
<223> OTHER INFORMATION: dTrp
<220> FEATURE:
<221> NAME/KEY: MOD_RES
<222> LOCATION: (21)..(21)
<223> OTHER INFORMATION: 3' -NH2

<400> SEQUENCE: 10

Gly Ile Phe Ser Lys Leu Ala Gly Lys Lys Ile Lys Asn Leu Leu Ile
1               5                   10                  15

Trp Gly Leu Lys Gly
            20

<210> SEQ ID NO 11
<211> LENGTH: 21
<212> TYPE: PRT
<213> ORGANISM: Artificial Sequence
<220> FEATURE:
<223> OTHER INFORMATION: Synthetic: Esc 10
<220> FEATURE:
<221> NAME/KEY: MOD_RES
<222> LOCATION: (14)..(14)
<223> OTHER INFORMATION: dLeu
<220> FEATURE:
<221> NAME/KEY: MOD_RES
<222> LOCATION: (21)..(21)
<223> OTHER INFORMATION: 3' -NH2

<400> SEQUENCE: 11

Gly Ile Phe Ser Lys Leu Ala Gly Lys Lys Ile Lys Asn Leu Leu Ile
1               5                   10                  15

Trp Gly Leu Lys Gly
            20
```

USE OF ESCULENTIN AND ITS DERIVATIVES FOR USE IN THE TREATMENT OF CYSTIC FIBROSIS

RELATED APPLICATIONS

This application is a national phase application claiming benefit of priority under 35 U.S.C. § 371 to Patent Convention Treaty (PCT) International Application serial number PCT/EP2020/078394, filed Oct. 9, 2020, now pending, which claims the benefit of priority to Italian patent No. 102019000018938 filed on Oct. 16, 2019. The aforementioned applications are expressly incorporated herein by reference in their entirety and for all purposes.

REFERENCE TO SEQUENCE LISTING

This application includes an electronically submitted sequence listing in .txt format. The .txt file contains a sequence listing entitled "5582.148681_ST25.txt" created on May 27, 2022 and is 5,248 bytes in size. The sequence listing contained in this .txt file is part of the specification and is hereby incorporated by reference herein in its entirety.

BACKGROUND OF THE INVENTION

The present invention refers to the field of pharmacology since it describes the use of esculentin and its derivatives for use in the treatment of cystic fibrosis.

STATE OF THE ART

Cystic Fibrosis (CF) is an autosomal recessive genetic disease which affects approximately 1 in 2500 new births of Caucasian population [Cuthbert A W (2011) New horizons in the treatment of cystic fibrosis. Br J Pharmacol 163, 173-183]. It is characterized by mutations in the gene encoding the CF transmembrane conductance regulator (CFTR); a chloride channel which is mainly expressed at the apical plasma membrane of secretory epithelia [Sheppard D N, Welsh M J (1999) Structure and function of the CFTR chloride channel. Physiol Rev 79, S23-45]. CFTR bears two transmembrane domains and two nucleotide-binding regions (NBD1 and NBD2) connected by a regulatory portion [Riordan J R, Rommens J M, Kerem B, Alon N, Rozmahel R, Grzelczak Z, Zielenski J, Lok S, Plavsic N, Chou J L, et al. (1989) Identification of the cystic fibrosis gene: cloning and characterization of complementary DNA. Science 245, 1066-1073]. Phosphorylation at multiple sites in the regulatory domain, by cAMP-dependent protein kinase A (PKA) [Cheng S H, Rich D P, Marshall J, Gregory R J, Welsh M J, Smith A E (1991) Phosphorylation of the R domain by cAMP-dependent protein kinase regulates the CFTR chloride channel. Cell 66, 1027-1036], as well as interaction with ATP at the two NBDs, control channel opening [Anderson M P, Welsh M J (1992) Regulation by ATP and ADP of CFTR chloride channels that contain mutant nucleotide-binding domains. Science 257, 1701-1704; Smit L S, Wilkinson D J, Mansoura M K, Collins F S, Dawson D C (1993) Functional roles of the nucleotide-binding folds in the activation of the cystic fibrosis transmembrane conductance regulator. Proc Natl Acad Sci USA 90, 9963-9967.]. Differently, ATP hydrolysis at NBD2 induces channel closing [Carson M R, Travis S M, Welsh M J (1995) The two nucleotide-binding domains of cystic fibrosis transmembrane conductance regulator (CFTR) have distinct functions in controlling channel activity. J Biol Chem 270, 1711-1717].

Airway epithelium forms a cellular monolayer where cells are connected to each other via intercellular junctions that differ in their morphological appearance, composition and function. The tight junction or zona occludens is the intercellular junction that regulates diffusion of water and solutes and allows adjacent cells to form selectively permeable cellular barriers that separate apical and basolateral sides in the bronchial tree, thereby controlling the transport processes between the apical and basolateral compartments to maintain airway homeostasis. Barrier integrity is vital for the physiological activities of the tissue and can be assessed by measurement of transepithelial/transendothelial electrical resistance (TEER) across a cellular monolayer [Srinivasan B, Kolli A R, Esch M B, Abaci H E, Shuler M L, Hickman J J (2015) TEER measurement techniques for in vitro barrier model systems. J Lab Autom 20, 107-126].

The most prevalent CF-associated mutation is the loss of phenylalanine 508 in the NBD1 (F508del CFTR). This causes an incorrectly folded protein that is rapidly degraded by proteasome-dependent manner [Jensen T J, Loo M A, Pind S, Williams D B, Goldberg A L, Riordan J R (1995) Multiple proteolytic systems, including the proteasome, contribute to CFTR processing. Cell 83, 129-135]. Because of this trafficking defeat, a small fraction of F508del CFTR reaches the plasma membrane [Pranke I M, Sermet-Gaudelus I (2014) Biosynthesis of cystic fibrosis transmembrane conductance regulator. Int J Biochem Cell Biol 52, 26-38]. Moreover, the mutated protein also exhibits a defect channel gating [Denning G M, Anderson M P, Amara J F, Marshall J, Smith A E, Welsh M J (1992) Processing of mutant cystic fibrosis transmembrane conductance regulator is temperature-sensitive. Nature 358, 761-764]. Among other CFTR mutations, the glycine-to aspartic acid change at codon 551 (G551D) is the third commonest mutation with a worldwide frequency in CF as high as 8% [Cashman S M, Patino A, Delgado M G, Byrne L, Denham B, De Arce M (1995) The Irish cystic fibrosis database. J Med Genet 32, 972-975]. It produces a protein that is well synthesized, processed and correctly inserted in the plasma membrane but with marked reduction in channel activity [Welsh M J, Smith A E (1993) Molecular mechanisms of CFTR chloride channel dysfunction in cystic fibrosis. Cell 73, 1251-1254].

As a consequence of such CFTR mutations, the secretion of chloride ions outside the cells is inhibited. This induces an increasing water absorption by epithelial cells and the formation of a sticky and dehydrated mucus layer on the airway epithelia which favors the entrapment and accumulation of inhaled microbes, including *Pseudomonas aeruginosa* [Dalemans W, Barbry P, Champigny G, Jallat S, Dott K, Dreyer D, Crystal R G, Pavirani A, Lecocq J P, Lazdunski M (1991) Altered chloride ion channel kinetics associated with the delta F508 cystic fibrosis mutation. Nature 354, 526-528]. Therefore, a chronic pulmonary infection is developed along with lung tissue damage and impairment of respiratory functions.

During the last years, CF research community has focused its attention on the identification and development of small molecules able to help trafficking/delivery of the mutated protein to the plasma membrane (namely correctors) and/or to improve ions permeation through CFTR channel (namely potentiators) [Odolczyk N, Fritsch J, Norez C, Servel N, da Cunha M F, Bitam S, Kupniewska A, Wiszniewski L, Colas J, Tarnowski K, Tondelier D, Roldan A, Saussereau E L, Melin-Heschel P, Wieczorek G, Lukacs G L, Dadlez M, Faure G, Herrmann H, Ollero M, Becq F, Zielenkiewicz P, Edelman A (2013) Discovery of novel potent DeltaF508-CFTR correctors that target the nucleotide binding domain. EMBO Mol Med 5, 1484-1501]. However, no compounds able to recover the complete CFTR functionality are available.

Studies conducted in our laboratory have led to the discovery of a frog-skin derived antimicrobial peptide (AMP), i.e. Esc(1-21) [Islas-Rodriguez A E, Marcellini L, Orioni B, Barra D, Stella L, Mangoni M L (2009) Esculentin 1-21: a linear antimicrobial peptide from frog skin with inhibitory effect on bovine mastitis-causing bacteria. J Pept Sci 15, 607-614], with a potent antipseudomonal activity [Luca V, Stringaro A, Colone M, Pini A, Mangoni M L (2013) Esculentin(1-21), an amphibian skin membrane-active peptide with potent activity on both planktonic and biofilm cells of the bacterial pathogen *Pseudomonas aeruginosa*. Cell Mol Life Sci 70, 2773-2786]. It is a cationic peptide at neutral pH with an alpha-helical structure in membrane mimicking environments and a mechanism of microbicidal action which is based on the perturbation of the bacterial membrane. This makes it more difficult for the bacteria to develop resistance compared to the single target-directed conventional antibiotics. We also demonstrated that by changing the configuration of only two L-amino acids in the sequence of Esc(1-21), i.e. Ser14 and Leu17 with the corresponding D-enantiomers, the resulting diastereomer Esc(1-21)-1c was more resistant to proteolytic degradation; more efficient to induce re-epithelialization of bronchial epithelial cells expressing either a functional or a mutated copy of CFTR (wt-CFBE and F508del-CFBE, respectively) in an in vitro wound-healing assay [Cappiello F, Di Grazia A, Segev-Zarko L A, Scali S, Ferrera L, Galietta L, Pini A, Shai Y, Di Y P, Mangoni M L (2016) Esculentin-1a-Derived Peptides Promote Clearance of *Pseudomonas aeruginosa* Internalized in Bronchial Cells of Cystic Fibrosis Patients and Lung Cell Migration: Biochemical Properties and a Plausible Mode of Action. Antimicrob Agents Chemother 60, 7252-7262]; more active against *P. aeruginosa* biofilm [Di Grazia A, Cappiello F, Cohen H, Casciaro B, Luca V, Pini A, Di Y P, Shai Y, Mangoni M L (2015) D-Amino acids incorporation in the frog skin-derived peptide esculentin-1a (1-21)NH2 is beneficial for its multiple functions. Amino Acids 47, 2505-2519; Casciaro B, Cappiello F, Cacciafesta M, Mangoni M L (2017) Promising Approaches to Optimize the Biological Properties of the Antimicrobial Peptide Esculentin-1a(1-21)NH2: Amino Acids Substitution and Conjugation to Nanoparticles. Front Chem 5, 26]; and more potent in reducing lung bacterial burden in murine models of *Pseudomonas* lung infection upon a single intra-tracheal instillation at a very low dosage (0.1 mg/kg corresponding to 20 μM) with negligible toxicity or inflammatory side events. Furthermore, we also showed how polyvinyl alcohol engineered poly(lactic-co-glycolic) acid (PLGA) nanoparticles represent an enticing nanoformulation for pulmonary delivery of Esc(1-21) and Esc(1-21)-1c (Esc peptides) prolonging their therapeutic efficacy against *Pseudomonas*-induced lung infection [Chen C, Mangoni M L, Di Y P (2017) In vivo therapeutic efficacy of frog skin-derived peptides against *Pseudomonas aeruginosa*-induced pulmonary infection. Sci Rep 7, 8548].

US patent application n. US2017166614 discloses an esculentin-2CHa peptide and analogues thereof, and the use each thereof in the treatment of diabetes, for example type 2 diabetes; insulin resistance; obesity, and/or hypercholesterolemia, and pharmaceutical composition thereof.

U.S. Pat. No. 6,107,335 discloses 18 beta, 19 beta-diacetyloxy-18 alpha, 19 alpha-epoxy-3, 13(16), 14-clerodatrien-2-one (Esculentin A) and 18 beta, 19 beta-diacetyloxy-18 alpha, 19 alpha-epoxy-3,12,14-clerodatrien-2 beta-isovaleryloxy-6 beta, 7 alpha-diol (Esculentin B) obtained from plants belonging to the Samydaceae family, particularly Casearia *esculenta*, for use in the manufacture of medicaments useful as anti-inflammatory and/or anti-cancer agents.

U.S. Pat. No. 10,059,752 and US patent application, publication n. US2018361010, of the same inventor of the present application, disclose antibacterial peptides Esculentin Esc(1-21) and diastereomer Esc(1-2)-1c, pharmaceutical compositions thereof and their use for reducing the severity of microbe-induced inflammation, for stimulating wound and devices having a surface with a coating comprising the synthetic antibacterial peptides.

The Proceedings of the 16th Italian Convention of Investigators in "Cystic Fibrosis", MULTIDISCIPLINARY RESPIRATORY MEDICINE, BIOMED CENTRAL LTD, LONDON, UK, vol. 14, no. 1, 6 Feb. 2019 (2019-02-06), pages 1-15, XP021270913, D01: 10.1186/S40248-018-0164-1, and Floriana Cappiello et al., "Esculentin-1a-derived peptides promote clearance of *P. aeruginosa* internalized in cystic fibrosis bronchial cells as well as lung cells migration: Biochemical properties and a plausible mode of action", ANTIMICROBIAL AGENTS AND CHEMOTHERAPY, 26 Sep. 2016 (2016-09-26), XP055680885, US ISSN: 0066-4804, D01: 10.1128/AAC.00904-16 disclose the use of esculentin peptides for the treatment of *Pseudomonas aeruginosa* infection and its clearance in cystic fibrosis patients, in particular report the ability of the peptides in question to kill *P. aeruginosa* internalized in bronchial cells of CF patients and to stimulate migration of these cells also in the context of bacterial infection and therefore their plausible help in promoting recovery of the bronchial epithelial integrity

Technical Problem

The inventors of the present invention investigated the effect of Esculentin Esc(1-21) and diastereomer Esc(1-2)-1c on the ion currents controlled by CFTR by measuring TEER in wt-CFBE and cell lines expressing CFTR gating mutations as well as in primary airway epithelial cells, and by Ussing chamber experiments to confirm the data. Unexpectedly, the inventors of the present invention found out that Esc peptides have the capability to restore and improve the functionality of a mutated CFTR by acting as modulators.

The prior art suggest that in the sub-set of patients with cystic fibrosis, Esc peptides stimulate the migration of bronchial cells, promote clearance of *P. aeruginosa* internalized in cystic fibrosis bronchial cells and help recovery from pulmonary infections.

Cistic fibrosis is a genetic disease characterised by specific mutations in the gene encoding the CF transmembrane conductance regulator (CFTR), the chloride channel expressed at the apical plasma membrane of secretory epithelia, and the inventors found that esculentin affect directly the functionality of the mutated ion channel protein.

Said effect could not be derived from the prior art.

OBJECT OF THE INVENTION

The above technical problem is solved by providing a pharmaceutical composition comprising Esculentin-1a(1-21)NH$_2$ of SEQ ID NO: 2 GIFSKLAGKKIKNLLISGLKG- NH$_2$ and/or Esculentin diastereomer Esc(1-21)-1c of SEQ ID NO: 3 GIFSKLAGKKIKNLLISGLKG-NH$_2$ as active ingredient and pharmaceutically acceptable adjuvants and/or vehicles and/or excipients for use for restoring dysregulation of water and ions composition of periciliary liquid due to mutations of the CFTR gene encoding for Cystic fibrosis transmembrane conductance regulator (CFTR).

Another object of the present invention is a pharmaceutical composition comprising Esculentin-1a(1-21)NH$_2$ of SEQ ID NO: 2 GIFSKLAGKKIKNLLISGLKG-NH$_2$ and/or Esculentin diastereomer Esc(1-21)-1c of SEQ ID NO: 3 GIFSKLAGKKIKNLLISGLKG-NH$_2$ as active ingredient and pharmaceutically acceptable adjuvants and/or vehicles and/or excipients for use for the treatment of cystic fibrosis.

DETAILED DESCRIPTION OF THE INVENTION

Figure 1:
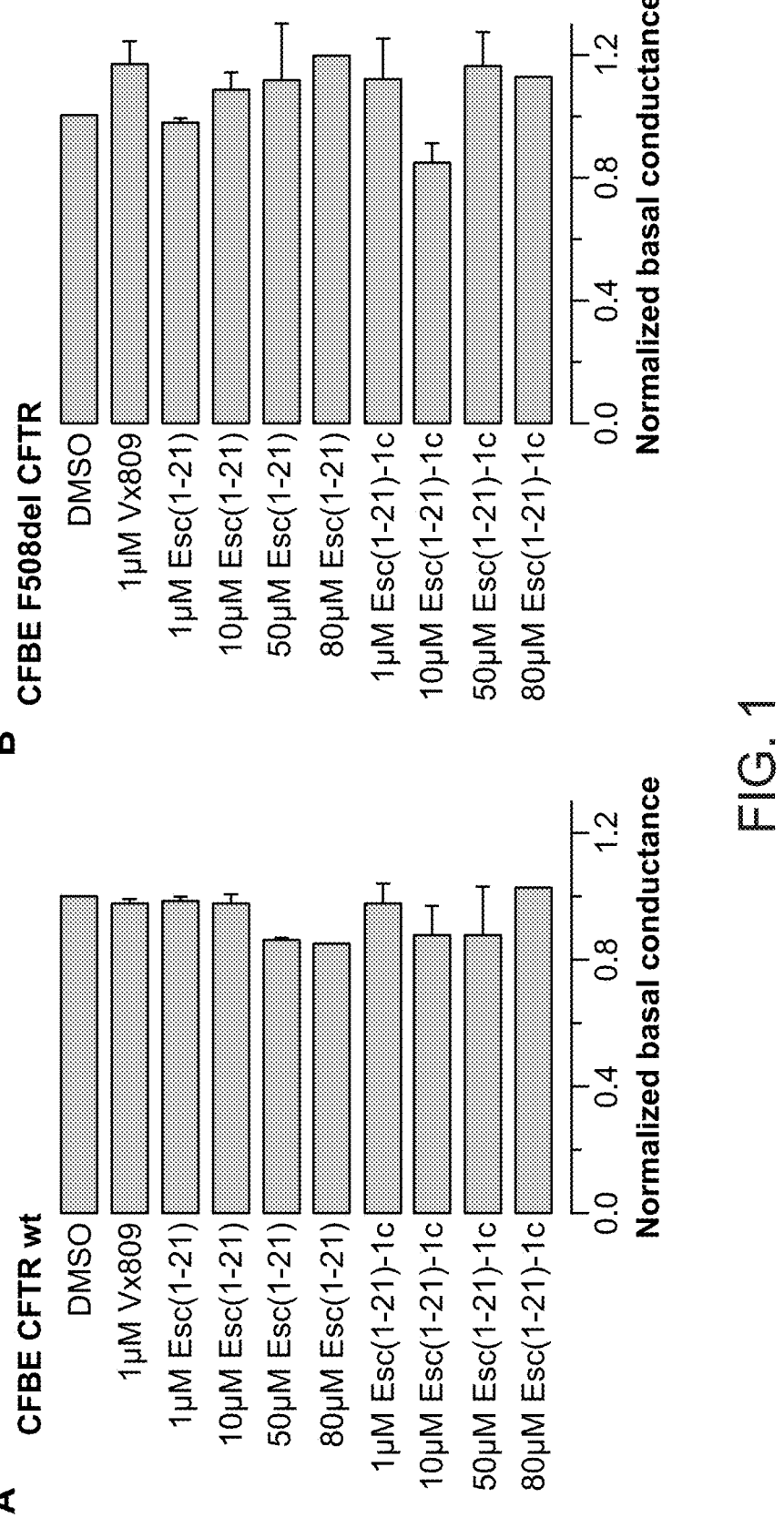
FIG. 1 shows in panel A wt-CFBE and in panel B F508del-CFBE epithelial integrity measured by the TEER assay after 24 h treatment with the indicated peptides at different concentrations. Basal conductance for each treatment was normalized to that of control cells (cells treated with 0.1% DMSO). Data are expressed as mean±SEM from three independent experiments. No significant differences were found. The corrector Vx-809 (1 µM) was used for comparison.

Within the meaning of the present invention Esculentin 1a is a naturally occurring peptide found in the skin of the amphibian *Pelophylax lessonae/ridibundus* (*Rana esculenta*). It is 46 amino acids in length and has an intramolecular disulphide bridge at the C-terminal end.

Esc-1a(1-21)NH$_2$ consists of the first 20 amino acids of the mature Esculentin 1a sequence with a glycinamide residue at the C-terminus.

```
Esculentin 1a:
                                    SEQ ID NO: 1
GIFSKLAGKKIKNLLISGLKNVGKEVGMDVVRTGIDIAGCKIKGEC;

Esculentin-1a (1-21) NH₂:
                                    SEQ ID NO: 2
GIFSKLAGKKIKNLLISGLKG-NH₂
```

Within the meaning of the present invention diastereomer Esc(1-21)-1c results by changing the configuration of only two L-amino acids in the sequence of Esc(1-21), i.e. Ser14 and Leu17 with the corresponding D-enantiomers.

```
            diastereomer Esc(1-21)-1c
                                    SEQ ID NO: 3
            GIFSKLAGKKIKNLLISGLKG-NH₂
```

Within the meaning of the present invention the Cystic fibrosis transmembrane conductance regulator (CFTR) is a ABC transporter-class ion channel protein that conducts chloride ions across epithelial cell membranes that is encoded by the CFTR gene, the mutations of the CFTR gene affecting chloride ion channel function lead to dysregulation of epithelial fluid transport in pancreas and lung epithelium which leads to cystic fibrosis.

Within the meaning of the present invention periciliary liquid means the liquid, containing water and ions, wetting cilia of the respiratory epithelium (or airway epithelium), the latter being a ciliated columnar epithelium lining the respiratory tract. Dysregulation of the content and/or composition of water and/or ions of the periciliary liquid is due to mutations of the CFTR gene encoding for Cystic fibrosis transmembrane conductance regulator (CFTR).

Within the meaning of the present invention a modulator of Cystic fibrosis transmembrane conductance regulator (CFTR) is a compound able to improve the chloride ions flow through CFTR. A modulator may be selected from the group consisting of: Ivacaftor, Lumacaftor, Tezacaftor, VX-445, VX-659, VX-152, VX-440, VX-561 (CTP-656), QBW251, FDL169, GLPG1837, GLPG2222, GLPG2451, GLPG2737, GLPG3067, GLPG3067, PTI-428, PTI-801, PTI-808, QR-010, MRT5005, QBW276, SPX-101, AZD5634, BI 443651, or mixture thereof (Martina Gentzsch, and Marcus A. Mall, Ion Channel Modulators in Cystic Fibrosis, CHEST, 2018; 154(2):383-393).

Object of the present invention is a pharmaceutical composition comprising Esculentin-1a(1-21)NH$_2$ of SEQ ID NO: 2 GIFSKLAGKKIKNLLISGLKG-NH$_2$ and/or Esculentin diastereomer Esc(1-21)-1c of SEQ ID NO: 3 GIFSK-LAGKKIKNLLISGLKG-NH$_2$ as active ingredient and pharmaceutically acceptable adjuvants and/or vehicles and/or excipients for use for restoring dysregulation of water and/or ions content and/or composition of the periciliary liquid.

Another object of the present invention is a pharmaceutical composition comprising Esculentin-1a(1-21)NH$_2$ of SEQ ID NO: 2 GIFSKLAGKKIKNLLISGLKG-NH$_2$ and/or Esculentin diastereomer Esc(1-21)-1c of SEQ ID NO: 3 GIFSKLAGKKIKNLLISGLKG-NH$_2$ as active ingredient and pharmaceutically acceptable adjuvants and/or vehicles and/or excipients for use for the treatment of cystic fibrosis.

Preferably the active ingredient is Esc(1-21)-1c of SEQ ID NO: 3.

Optionally the pharmaceutical composition comprising Esculentin-1a(1-21)NH$_2$ of SEQ ID NO: 2 GIFSKLAGK-KIKNLLISGLKG-NH$_2$ and/or Esculentin diastereomer Esc (1-21)-1c of SEQ ID NO: 3 GIFSKLAGKKIKNLLIS-GLKG-NH$_2$ as active ingredient and pharmaceutically acceptable adjuvants and/or vehicles and/or excipients further comprises a modulator of Cystic fibrosis transmembrane conductance selected from the group consisting of: Ivacaftor, Lumacaftor, Tezacaftor, VX-445, VX-659, VX-152, VX-440, VX-561 (CTP-656), QBW251, FDL169, GLPG1837, GLPG2222, GLPG2451, GLPG2737, GLPG3067, GLPG3067, PTI-428, PTI-801, PTI-808, QR-010, MRT5005, QBW276, SPX-101, AZD5634, BI 443651, or mixture thereof.

The pharmaceutical compositions can be prepared by conventional methods and techniques which are common practice in the pharmaceutical industry, such as, for example, those illustrated in Remington's Pharmaceutical Science Handbook, Mack Pub. N.Y.—last edition.

The compositions according to the present invention contain, along with the active ingredient, at least one pharmaceutically acceptable vehicle or excipient. These may be particularly useful formulation coadjuvants, e.g. solubilising agents, dispersing agents, suspension agents, and emulsifying agents.

The invention also provides a method for the treatment of Cystic fibrosis in a patient in need thereof by administering a pharmaceutically active amount of a pharmaceutical composition comprising Esculentin-1a(1-21)NH2 of SEQ ID NO: 2 GIFSKLAGKKIKNLLISGLKG-NH2 and/or Esculentin diastereomer Esc(1-21)-1c of SEQ ID NO: 3 GIFSK-LAGKKIKNLLISGLKG-NH2 as active ingredient and pharmaceutically acceptable adjuvants and/or vehicles and/ or excipients and optionally a modulator of Cystic fibrosis transmembrane conductance selected from the group consisting of: Ivacaftor, Lumacaftor, Tezacaftor, VX-445, VX-659, VX-152, VX-440, VX-561 (CTP-656), QBW251, FDL169, GLPG1837, GLPG2222, GLPG2451, GLPG2737, GLPG3067, GLPG3067, PTI-428, PTI-801, PTI-808, QR-010, MRT5005, QBW276, SPX-101, AZD5634, BI 443651, or mixture thereof.

EXAMPLES

Materials and Methods

Primary human bronchial epithelial cells derived from CF and non-CF individuals were provided by the Italian Cystic fibrosis Foundation (FFC) Cell Culture Service, while the immortalized human bronchial epithelial cells were obtained from a CF patient (CFBE41o-) and subsequently transduced with a lentiviral vector for a stable expression of the functional CFTR or F508delCFTR (wt-CFBE and F508del-CFBE, respectively) [Bebok Z, Collawn J F, Wakefield J, Parker W, Li Y, Varga K, Sorscher E J, Clancy J P (2005) Failure of cAMP agonists to activate rescued deltaF508 CFTR in CFBE41o- airway epithelial monolayers. J Physiol 569, 601-615]. Human bronchial epithelial cells were cultured in flasks in proliferative serum-free medium containing 1:1 mixture of RPMI 1640 and LHC basal medium (Life Technologies, Monza, Italy) supplemented with various hormones and supplements, 100 U/ml penicillin and 100 µg/ml streptomycin and then seeded on porous membranes (12 mm Snapwell inserts, Corning, code 3801 for using chamber studies, or 0.33 cm$^2$ mini-transwell inserts, Corning, code 3379 for TEER measurement) as previously described [Scudieri P, Caci E, Bruno S, Ferrera L, Schiavon M, Sondo E, Tomati V, Gianotti A, Zegarra-Moran O, Pedemonte N, Rea F, Ravazzolo R, Galietta L J (2012) Association of TMEM16A chloride channel overexpression with airway goblet cell metaplasia. J Physiol 590, 6141-6155].

The immortalized bronchial epithelial cell lines (CFBE41o-) were cultured in minimal essential medium (MEM) and then seeded on porous membranes (0.33 cm$^2$ mini-transwell inserts, Corning, code 3379) for TEER measurements.

Fischer rat thyroid (FRT) cells with stable expression of mutated CFTR, were cultured in Coon's modified Ham's F-12 medium.

Both media (MEM and Coon's) were supplemented with 10% fetal calf serum (Sigma-Aldrich, St Louis, MO, USA), 2 mM 1-glutamine, 100 U/ml penicillin and 100 µg/ml streptomycin.

To evaluate the lung epithelia integrity, cell lines expressing mutated or functional CFTR, seeded in permeable supports, were incubated for 24 h in their standard culture medium in the presence of peptides, at different concentration. Cells incubated with 0.1% Dimethylsulfoxide (DMSO) or with 1 µM of the corrector Vx-809 were included as controls. After 24 h, the medium was replaced with saline solution containing (in mM): 130 NaCl, 2.7 KCl, 1.5 KH$_2$PO$_4$, 1 CaCl$_2$, 0.5 MgCl$_2$, 10 glucose, 10 Na-Hepes (pH 7.4). Saline solution was added to both apical and basolateral compartments of the permeable supports. Samples were incubated for 10 minutes at 37° C. and TEER was measured in basal conditions without CFTR activation, with the epithelial voltohmeter (EVOM1, World Precision Instruments).

In parallel, to evaluate CFTR activation, the same saline solution was used. After measurement of basal TEER, 20

μM FSK+50 μM GEN as positive control, or FSK+ peptides at the desired concentration were added on the epithelium apical side. Finally, 30 μM PPQ102, a specific inhibitor of CFTR, was added on the epithelium apical side. After each addition, we waited ten minutes at 37° C. before measurement. From the values of TEER measured before and after CFTR inhibition, we calculated the CFTR-dependent trans-epithelial conductance for each condition [Sondo E, Falchi F, Caci E, Ferrera L, Giacomini E, Pesce E, Tomati V, Mandrup Bertozzi S, Goldoni L, Armirotti A, Ravazzolo R, Cavalli A, Pedemonte N (2018) Pharmacological Inhibition of the Ubiquitin Ligase RNF5 Rescues F508del-CFTR in Cystic Fibrosis Airway Epithelia. Cell Chem Biol 25, 891-905 e898].

For primary bronchial cells, Coon's modified Ham's F-12 medium supplemented with 20 mM Hepes was used for TEER measurements to evaluate CFTR activation. More precisely, after initial measurements at inactive CFTR, 10 μM amiloride, a specific inhibitor of epithelial sodium channel (ENaC) was added to the apical side of epithelia pre-incubated with 1 μM Vx-809. Subsequently, 20 μM FSK+50 μMGEN, as positive control, or FSK+peptides at the desired concentration were added. Finally, 30 μM PPQ102 was added on the epithelium apical side. After each addition, we waited ten minutes at 37° C. before measurement as indicated above.

Snapwell inserts (Corning 3801) carrying differentiated bronchial epithelia were mounted in a vertical diffusion chamber, resembling a Ussing chamber with internal fluid circulation. Both apical and basolateral chambers were filled with 5 ml of saline solution. The short-circuit current was recorded with a PowerLab 4/25 (ADInstruments) analog-to-digital converter connected to a computer. Epithelia were incubated for 24 h with 1 μM Vx-809 or 0.1% DMSO. Afterwards, 10 μM amiloride was added; subsequently, CFTR channels were activated by phosphorylation upon addition of 100 μM cpt-cAMP (permeable cAMP analog). Then, 1 μM of the potentiator Vx-770 as well as each Esc peptide was added on the epithelium apical side, as indicated. Finally, 10 μM Inh172, a specific inhibitor of CFTR was added to the epithelium apical side. Measurements were done after 5 min from the addition of each substance. In parallel, epithelia pre-incubated for 24 h with each peptide and then treated with amiloride, cpt-cAMP and Vx-770 were used for comparison.

FRT cells expressing G551D mutated CFTR and the halide-sensitive yellow fluorescent protein (YFP) were washed with PBS [Galietta L V, Jayaraman S, Verkman A S (2001) Cell-based assay for high-throughput quantitative screening of CFTR chloride transport agonists. Am J Physiol Cell Physiol 281, C1734-1742]. Cells were then incubated for 20 min with 60 μl of PBS plus FSK (20 μM) and GEN (50 μM) or with FSK+ Esc peptide (10 μM) to stimulate mutated CFTR. Cells were then transferred to a microplate reader for CFTR activity determination. The plate reader was equipped with high-quality excitation (HQ500) and emission (HQ535) filters for YFP. Each assay comprised a continuous 14-sec fluorescence reading, 2 sec before and 12 sec after injection of 165 μl of an iodide-containing solution (PBS with Cl– replaced by I-; final I-concentration 137 mM). Fluorescence of blank samples (without cells) was subtracted from values of all samples and normalized to the initial background fluorescence. To determine I-influx rate, the data corresponding to the final 11 sec measurements for each well were fitted with an exponential function to extrapolate initial slope (quenching rate, QR).

Quantitative data derived from independent experiments were expressed as the mean±standard error of the mean (SEM). Statistical significance was determined using Student's t test, with Igor environment (Wavemetrics, Lake Oswego, OR). P values of <0.05 were assumed to be statistically significant.

Peptides' Effect on Lung Epithelial Permeability

We initially tested whether Esc peptides affected the lung epithelial integrity by measuring the trans-epithelial electrical conductance in wt-CFBE and F508del-CFBE polarized epithelia, 24 h after peptide incubation at different concentrations (1 μM, 10 μM, 50 μM and 80 μM). The corrector Vx-809 (1 μM) was used for comparison. As reported in FIG. 1, no significant change in the trans-epithelial electrical conductance was obtained in comparison to DMSO-treated control samples, indicating that both peptides are not expected to affect the pulmonary epithelial entirety.

Potentiator Activity of Peptides on the Mutated CFTR

Figure 2:
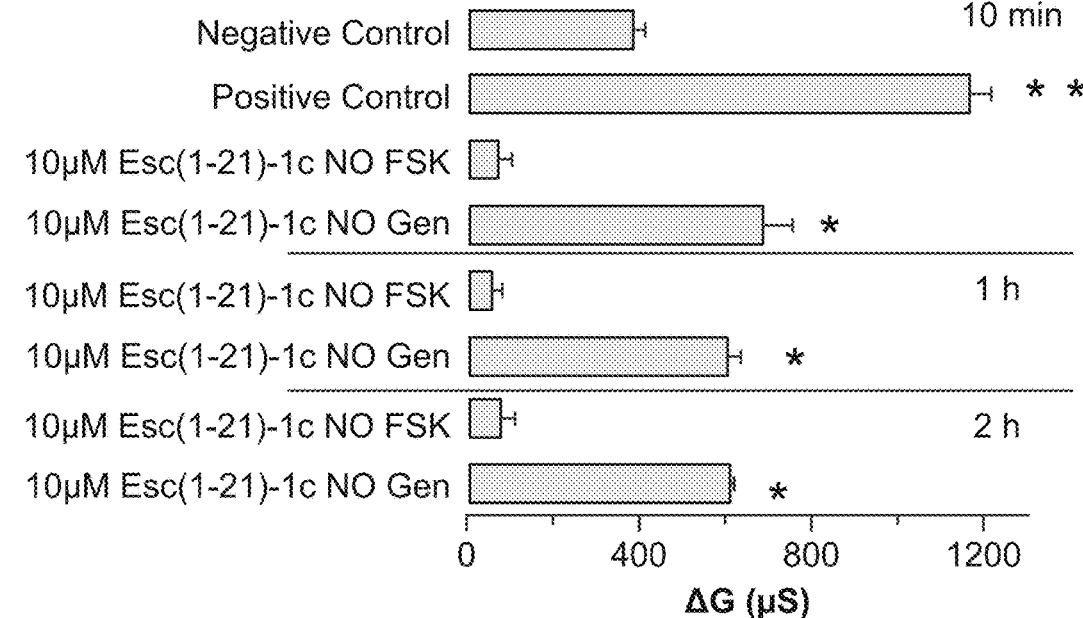
FIG. 2 shows in panel A the time course of the potentiator effect of Esc(1-21)-1c on F508del-CFTR activity. After pre-incubation of cells for 24 h with 1 µM Vx-809, CFTR conductance was measured after 10 min, 1 h and 2 h addition of peptide plus 20 µM Forskolin (FSK) or 50 µM Genistein (GEN). Cells pre-incubated with 0.1% DMSO or 1 µM Vx-809 and then treated with FSK+GEN were used as negative and positive controls, respectively. In panel B the potentiator activity of Esc(1-21) and Esc(1-21)-1c (10 µM) after 10 min of peptide addition in the presence of 20 µM FSK. Data are expressed as mean±SEM from three independent experiments. The levels of statistical significance of samples versus the negative control, are P values <0.01 (*) and <0.001 (**).
Figure 2:
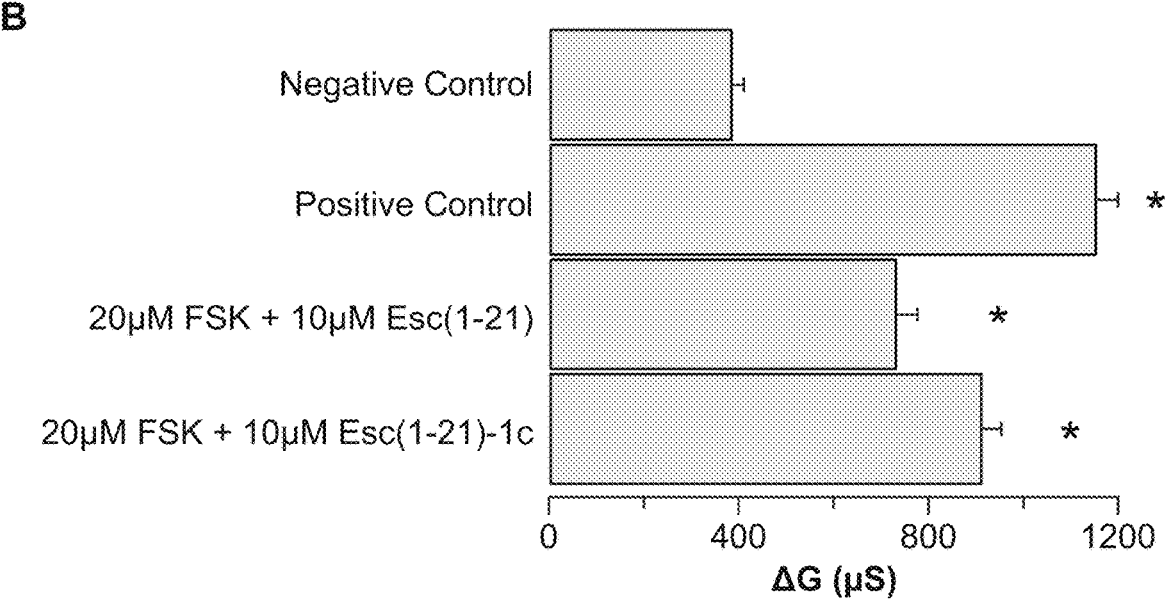

Subsequently, was investigated the ability of Esc peptides to act as potentiators of mutated CFTR, by promoting its phosphorylation state or its channel opening time, mimicking the activity of forskolin (FSK) or genistein (GEN), respectively, which are both needed for full activation of CFTR [Sondo E, Falchi F, Caci E, Ferrera L, Giacomini E, Pesce E, Tomati V, Mandrup Bertozzi S, Goldoni L, Armirotti A, Ravazzolo R, Cavalli A, Pedemonte N (2018) Pharmacological Inhibition of the Ubiquitin Ligase RNF5 Rescues F508del-CFTR in Cystic Fibrosis Airway Epithelia. Cell Chem Biol 25, 891-905 e898]. Noteworthy, the adenylate cyclase activator FSK [Ma T, Thiagarajah J R, Yang H, Sonawane N D, Folli C, Galietta L J, Verkman A S (2002) Thiazolidinone CFTR inhibitor identified by high-throughput screening blocks cholera toxin-induced intestinal fluid secretion. J Clin Invest 110, 1651-1658] is reported to trigger an increase of intracellular cAMP favouring CFTR phosphorylation by cellular protein kinases e.g. PKA, while the isoflavone GEN accelerates channel opening, by promoting NBD dimerization, and slows channel closure by stabilizing the NBD1:NBD2 dimer conformation [Schmidt A, Hughes L K, Cai Z, Mendes F, Li H, Sheppard D N, Amaral M D (2008) Prolonged treatment of cells with genistein modulates the expression and function of the cystic fibrosis transmembrane conductance regulator. Br J Pharmacol 153, 1311-1323]. The CFTR-mediated conductance of bronchial epithelium was evaluated by TEER, after 10 min, 1 h and 2 h treatment of F508del-CFBE (pre-incubated with the corrector Vx-809 in order to trigger the mutated protein to the apical membrane) with Esc(1-21)-1c (10 μM), in the absence of FSK or GEN. Interestingly, in the absence of FSK, no rescue of CFTR activity was achieved. In contrast, a significant increase of CFTR conductance was measured when Esc(1-21)-1c was incubated with FSK without GEN, already after 10 min of peptide treatment. This clearly denoted that the peptide was able to potentiate CFTR activity, likely by prolonging its channel opening time. The potentiator activity of Esc(1-21)-1c in the absence of GEN was also examined after 1 h or 2 h treatment and found to remain constant up to 2 h (FIG. 2A). The comparison between Esc(1-21)-1c and the all-L Esc(1-21), after 10 min treatment at 10 μM is reported in FIG. 2B.

Figure 3:
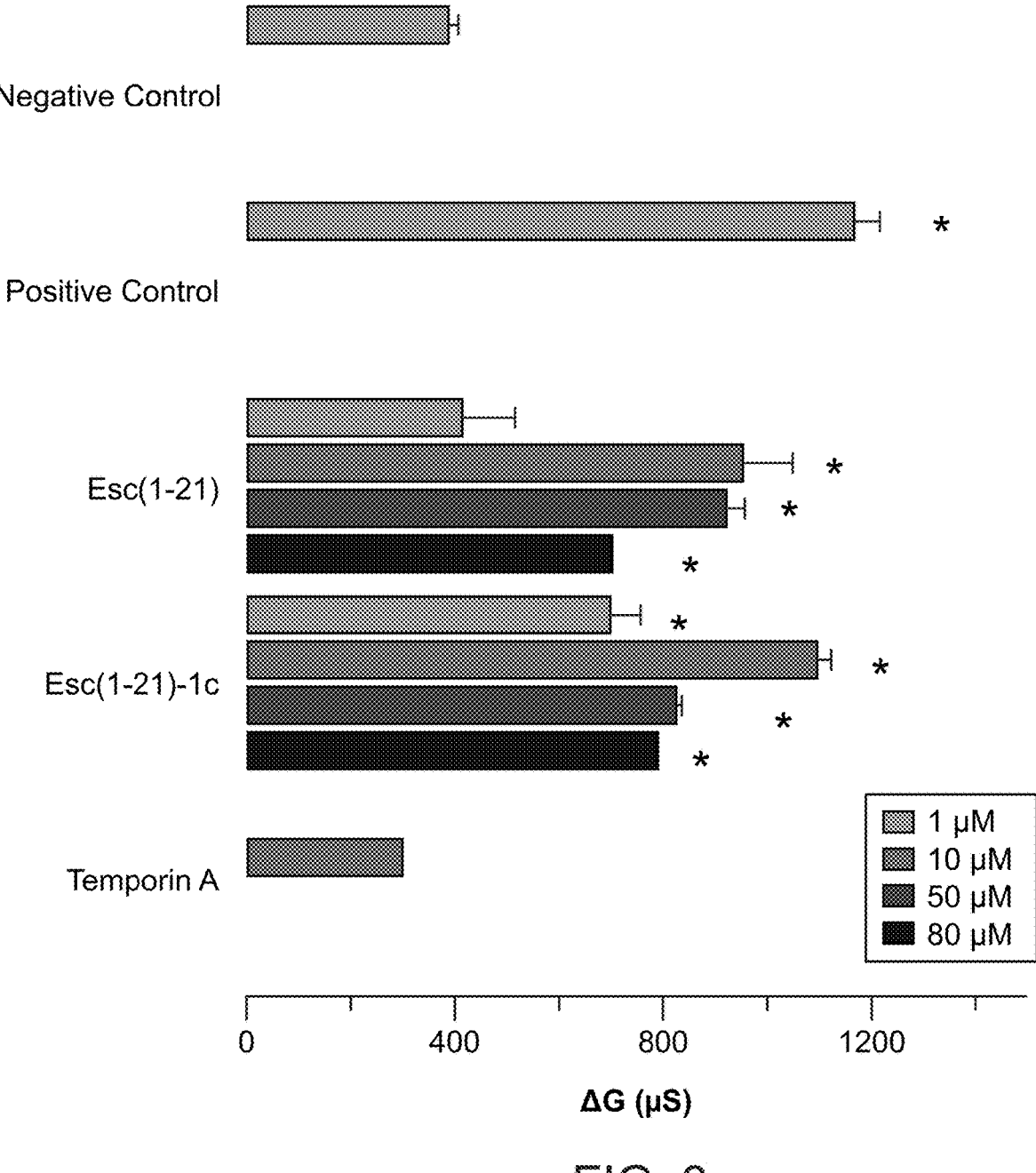
FIG. 3 shows the dose-response effect of Esc peptides on the CFTR-trans-epithelial conductance measured with TEER assay. The peptide temporin A was also included for comparison. Negative or positive controls were cells treated with 0.1% DMSO or 1 µM Vx-809 and subsequently stimulated with FSK+GEN. Data are expressed as mean±SEM, from three independent experiments. The level of statistical significance of samples versus the negative control is P value <0.01 (*).

Dose-Response Effect of Peptides on F508Del-CFTR Expressed in Bronchial Cell Lines The conductance was then measured on F508del-CFBE. After pre-incubation with Vx-809 and CFTR activation by FSK+GEN for 10 min, or by FSK+Esc peptides at different concentration. A higher boost in the conductance level of CFTR was induced by both peptides at 10 μM (and was comparable to that provoked by the full activation of CFTR with FSK+GEN (positive control). The results could not be ascribed to the membrane-perturbing activity of Esc peptides, since no effect on CFTR currents was observed when the membrane-active AMP temporin A (10 μM) was used (FIG. 3).

Effect of Peptides on CFTR Activity in Primary Airway Epithelial Cells

Figure 4:
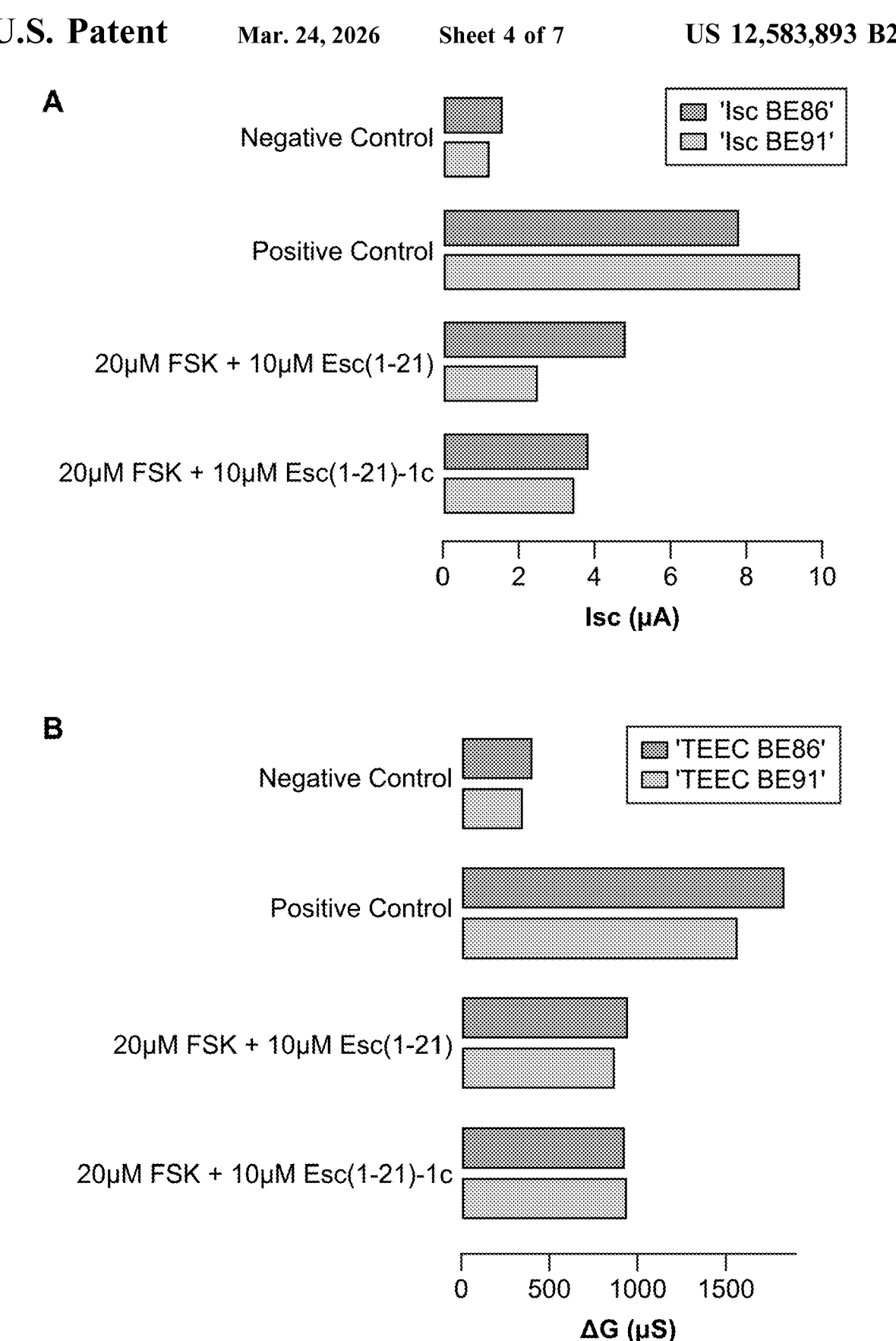
FIG. 4 shows the TEER measurements performed on human primary bronchial epithelia derived from two different CF patients homozygous for the F508del mutation. After 24 h treatment with Vx-809 (1 µM), epithelia were stimulated with FSK+GEN or with FSK+ peptide as indicated, for 10 min. The graph bars show the delta between the values of electrical resistance measured before and after CFTR inhibition, subsequently converted into its reciprocal conductance (panel A), and the equivalent short-circuit current (panel B). Cells pre-incubated with 0.1% DMSO or 1 µM Vx-809 and then treated with FSK+GEN were used as negative and positive controls, respectively.

On the basis of these encouraging data, was also analyzed the effect of both Esc peptides at their optimal concentration, i.e. 10 μM, on primary bronchial cells, derived from two different CF patients homozygous for F508del mutation, by TEER, after incubation with Vx-809. TEER and potential difference (DP) were measured before and after addition of amiloride (10 μM) to block epithelial sodium channel (ENaC)-mediated sodium absorption. The results indicated that both peptides improved CFTR activity with a slight difference on the two bronchial epithelia, likely due to own differences of CF patients (FIG. 4).

Ussing Experiments

Figure 5:
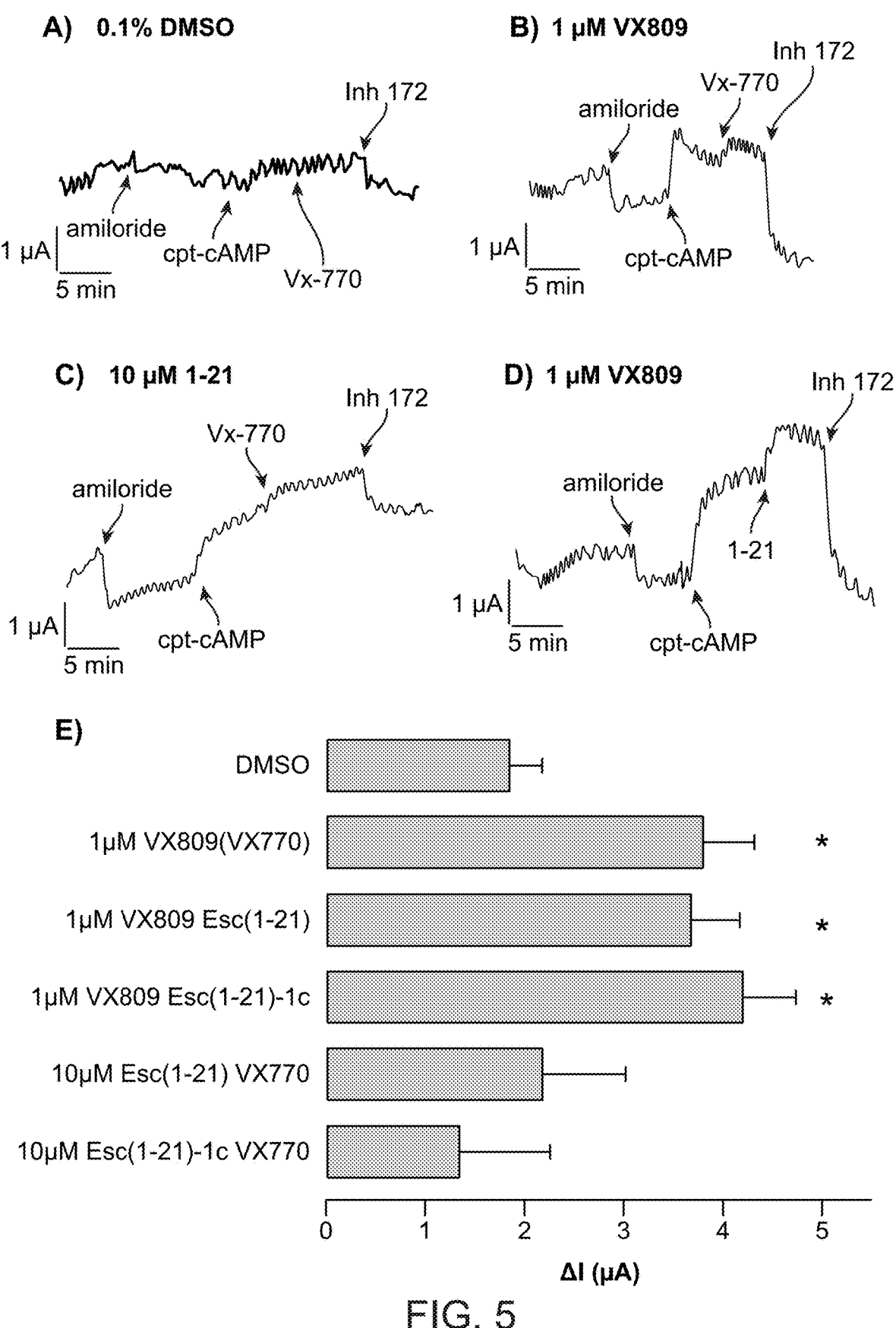
FIG. 5 shows the representative traces from Ussing chamber recordings of bronchial epithelial cells (HBE) derived from a homozygous F508del patient following a 24-h incubation with 0.1% DMSO (panel A), 1 µM Vx809 (panel B), 10 µM Esc(1-21) peptide (panel C) and subsequently treated with Vx-770 or following incubation with 1 µM Vx809 and treatment with Esc(1-21) (panel D). Bar graphs summarizing CFTR-mediated currents from Ussing chamber recordings of HBE after treatments are shown in panel E. Data are the mean±SEM from three independent experiments. The level of statistical significance versus DMSO-treated samples is P value <0.05 (*).

The CFTR potentiating activity of Esc peptides in primary airway epithelial cells was studied by Ussing chamber experiments on bronchial epithelia from homozygous F508del patient. Epithelia were treated for 24 h with 0.1% DMSO vehicle alone, 1 μM Vx809 or with each Esc peptide. Then, the samples were mounted in Ussing chambers for measurement of Cl⁻ secretion by short-circuit current analysis. After blocking Na⁺ current with amiloride, cells treated with DMSO vehicle alone or with Esc peptides showed only little CFTR function in response to the membrane permeant cAMP analog (cpt-cAMP) and the well-known potentiator VX-770 [Ma T, Thiagarajah J R, Yang H, Sonawane N D, Folli C, Galietta L J, Verkman A S (2002) Thiazolidinone CFTR inhibitor identified by high-throughput screening blocks cholera toxin-induced intestinal fluid secretion. J Clin Invest 110, 1651-1658], as pointed out by the small current increase (FIGS. 5A, C, E). This was also corroborated by the small current drop caused by the selective CFTR inhibition due to the addition of CFTR inhibitor 172 (inh-172). In contrast, when cells were incubated with Vx-809, a significant current increase was recorded upon addition of cpt-cAMP and Vx-770 or Esc peptides (FIGS. 5B, D, E), proving a consistent CFTR rescue activity. The results support the notion that both Esc peptides do not act as correctors of CFTR, but rather as efficient potentiators with a comparable activity to that of Vx-770.

Effect of Fragments of Esc Peptides on CFTR Activity

Figure 6:
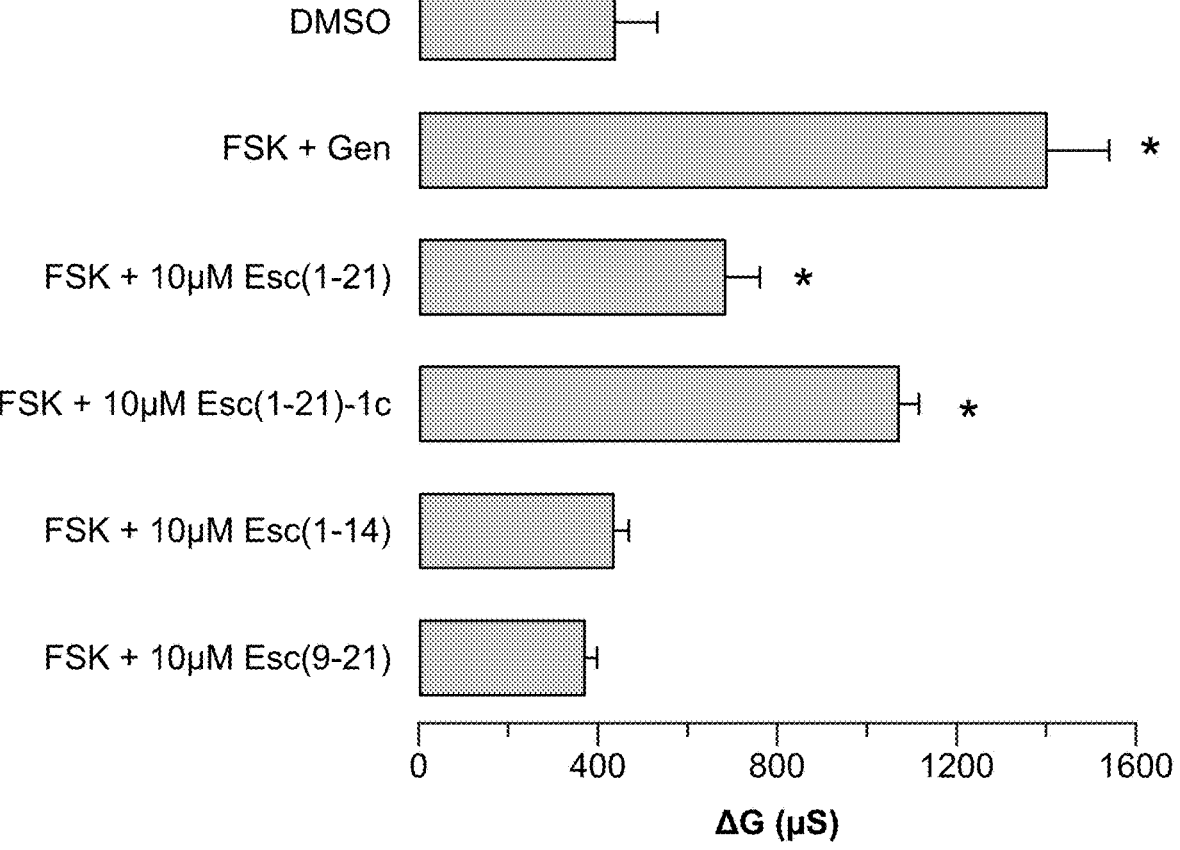
FIG. 6 shows the effect of Esc(1-14), Esc(9-21) fragments on the CFTR-transepithelial conductance measured with TEER assay compared to Esc(1-21) and its diastereomer. After 24 h treatment with Vx-809 (1 µM), epithelia were stimulated with FSK+ peptide as indicated, for 10 min. Data are expressed as mean±SEM from three independent experiments. Cells pre-incubated with 0.1% DMSO or with 1 µM Vx-809 and then treated with FSK+GEN were used as negative and positive controls, respectively. The level of statistical significance versus DMSO-treated samples is P value <0.05 (*).

In order to know whether shorter portions of Esc peptides were able to maintain the CFTR potentiator activity of the full length peptide, TEER experiments were performed on F508del-CFTR expressing bronchial cell lines, using the 1-14 and 9-21 fragments of Esc(1-21). However, as shown in FIG. 6, a negligible rescue of CFTR activity was recorded, highlighting that to restore the functionality of F508del-CFTR a full-length Esc peptide was needed.

Peptides' Effect on Other CFTR Gating Mutations

Figure 7:
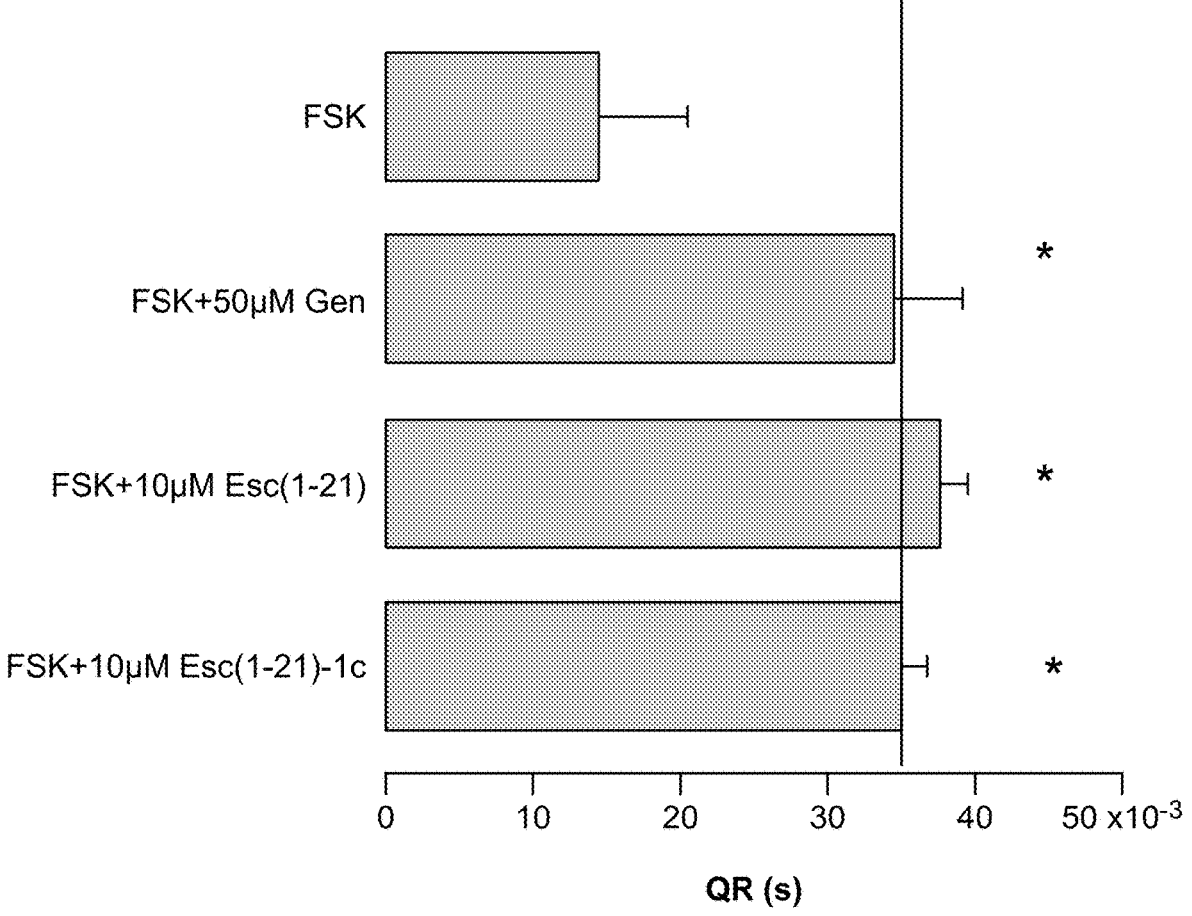
FIG. 7 shows the fluorescence quenching rate of cells expressing CFTR and YFP-H148Q after treatment with FSK+peptide, FSK+GEN or FSK alone and then exposed to iodide solution. Results are the mean of at least three independent experiments ±SEM. Assays were done at 37° C., and cells were incubated at this temperature for 5 min before starting the experiment. The level of statistical significance versus FSK-treated samples is P value <0.05 (*).

With the aim to verify whether the potentiator activity of Esc peptides could be enlarged to other CFTR gating mutation, the iodide influx was measured, expressed as fluorescence quenching rate, QR, in FRT cells expressing G551D-CFTR. The higher is the iodide influx, indicating the CFTR opening, the higher the QR. As reported in FIG. 7, the QR obtained when cells were stimulated with FSK plus each Esc peptide was similar to that found for the combination FSK+GEN and significantly higher than that provoked by FSK alone.

The results clearly supported a rescue of CFTR by Esc peptides also on epithelial cells expressing other gating mutation i.e. G551D.

The resulting high levels of resistance (low conductance), shown on FIG. 1 advised that the two peptides did not provoke any paracellular leakage of ions and that cell junctions were well tightened. Differently, a rapid raise of conductance was obtained when both peptides were added in the presence of FSK to the airway epithelium expressing F508del-CFTR, 24 h after pre-treatment with the corrector Vx-809, to trigger the CFTR channel to the apical membrane. Furthermore, the finding that upon administration of the selective inhibitor of CFTR (PPQ102), the conductance level went back to the initial value (before CFTR activation) highly pointed out that ions flux stimulated by our peptides is mediated by CFTR. Considering that a significant enhancement of CFTR conductance was recorded when the peptides were incubated with FSK without GEN (FIG. 2), this means that Esc peptides are able to potentiate the function of defective CFTR likely by acting as channel openers.

The ability of Esc peptides to restore the functionality of mutated CFTR was also confirmed by Ussing experiments on bronchial epithelium derived from a homozygous F508del patient. In this case, the difference between the ion current evaluated upon addition of the peptides to the activated channel and after its specific inhibition due to the CFTR inhibitor 172, was determined. A substantial drop of ion current was noted after administration of the selective CFTR inhibitor 172 to bronchial epithelium pretreated with Vx-809 and then exposed to cpt-cAMP and Esc peptides. Such outcome was similar to what found when the currently-used potentiator Vx-770 was employed instead of each Esc peptide.

TEER experiments are the common assays for an initial screening of molecules endowed with CFTR rescue activity, while Ussing experiments are usually performed to validate the data from the primary screening, according to Sondo E, Falchi F, Caci E, Ferrera L, Giacomini E, Pesce E, Tomati V, Mandrup Bertozzi S, Goldoni L, Armirotti A, Ravazzolo R, Cavalli A, Pedemonte N (2018) Pharmacological Inhibition of the Ubiquitin Ligase RNF5 Rescues F508del-CFTR in Cystic Fibrosis Airway Epithelia. Cell Chem Biol 25, 891-905 e898; Galietta L V, Jayaraman S, Verkman A S (2001) Cell-based assay for high-throughput quantitative screening of CFTR chloride transport agonists. Am J Physiol Cell Physiol 281, C1734-1742; Ma T, Thiagarajah J R, Yang H, Sonawane N D, Folli C, Galietta L J, Verkman A S (2002) Thiazolidinone CFTR inhibitor identified by high-through-put screening blocks cholera toxin-induced intestinal fluid secretion. J Clin Invest 110, 1651-1658; Schmidt A, Hughes L K, Cai Z, Mendes F, Li H, Sheppard D N, Amaral M D (2008) Prolonged treatment of cells with genistein modulates the expression and function of the cystic fibrosis transmembrane conductance regulator. Br J Pharmacol 153, 1311-1323; Tomati V, Caci E, Ferrera L, Pesce E, Sondo E, Cholon D M, Quinney N L, Boyles S E, Armirotti A, Ravazzolo R, Galietta L J, Gentzsch M, Pedemonte N (2018) Thymosin alpha-1 does not correct F508del-CFTR in cystic fibrosis airway epithelia. JCI Insight 3.

In summary, the results have clearly highlighted that besides displaying a well-known antibacterial activity, Esc peptides do also possess the capability to rescue the activity of CFTR expressing gating mutations (e.g. F508del-CFTR and G551D-CFTR), presumably by increasing the channel open probability. This effect is likely to involve a direct interaction and binding of the peptides to the NBDs of phosphorylated CFTR, favouring NBDs dimerization and channel gating, as already described for other CFTR activators, including GEN. It was also demonstrated that the entire sequence of Esc peptides is needed for that purpose.

Remarkably, these findings make Esc peptides attractive compounds for treatment of CF lung pathology by re-establishing the activity of mutated CFTR.

Role of Esc Peptides Sequence on the Activation of F508Del-CFTR

To understand whether the potentiator effect of Esc peptides was specifically dependent on their sequence and/or correlated to the presence of Ser17, eventually upon its phosphorylation by PKA, a series of peptide analogs bearing different L/D amino acids at position 17 were synthesized, the analogs are presented in the following table 1. The analogs were used to measure the trans-epithelial electrical conductance in Fish Rat Thyroid cells, which is a cell line frequently used for functional studies and stably expressing F508del-CFTR (del508-FRT). Among them, compounds 3 and 5 carrying L and D-Alanine, respectively; compound 6 carrying the achiral Glycine17; compounds 7 and 8, with another potential target amino acid of protein kinases i.e. D and L-threonine respectively; and compounds 9 ad 10 where Ser17 was replaced by a residue with a bulky side chain, i.e. D and L tryptophan, respectively. Furthermore, an analog with L-phosphoserine at position 17 were included for comparison. The data showed the transepithelial conductance measured after 10 min treatment of the epithelium with 10 µM of each peptide, tested as potentiator (instead of genistein) or with 20 µM FSK alone. With the exception of compound 2, carrying D-phosphoSer at position 17, incubation with all the other peptides or FSK did not significantly increase the function of F508del-CFTR, pointing out that (i) the potentiator effect of Esc peptides is a peculiar property of these molecules and that (ii) a Ser residue at position 17 plays a crucial role for this effect. The effect provoked by peptide 2 was higher than that of genistein when used at the same concentration of 10 µM.

TABLE 1

| Peptide | SEQ ID NO | Sequence |
|---|---|---|
| Esc (1-21) | 2 | Gly-Ile-Phe-Ser-Lys-Leu-Ala-10 Gly-Lys-Lys-Ile-Lys-Asn-Leu-20 Leu-Ile-Ser-Gly-Leu-Lys-Gly-NH2 |
| Esc (1-21)-1c | 3 | Gly-Ile-Phe-Ser-Lys-Leu-Ala-10 Gly-Lys-Lys-Ile-Lys-Asn-dLeu-Leu-Ile-20 dSer-Gly-Leu-Lys-Gly-NH2 |
| Esc 2 | 4 | Gly-Ile-Phe-Ser-Lys-Leu-Ala-10 Gly-Lys-Lys-Ile-Lys-Asn-dLeu-Leu-Ile-dphosphoSer-Gly-Leu-20 Lys-Gly-NH2 |

TABLE 1-continued

| Peptide | SEQ ID NO | Sequence |
|---|---|---|
| Esc 3 | 5 | Gly-Ile-Phe-Ser-Lys-Leu-Ala-10 Gly-Lys-Lys-Ile-Lys-Asn-dLeu-Leu-Ile-Ala-20 Gly-Leu-Lys-Gly-NH2 |
| Esc 5 | 6 | Gly-Ile-Phe-Ser-Lys-Leu-Ala-10 Gly-Lys-Lys-Ile-Lys-Asn-dLeu--Leu-Ile-20 dAla-Gly-Leu-Lys-Gly-NH2 |
| Esc 6 | 7 | Gly-Ile-Phe-Ser-Lys-Leu-Ala-10 Gly-Lys-Lys-Ile-Lys-Asn-dLeu--Leu-Ile-Gly-20 Gly-Leu-Lys-Gly-NH2 |
| Esc 7 | 8 | Gly-Ile-Phe-Ser-Lys-Leu-Ala-10 Gly-Lys-Lys-Ile-Lys-Asn-dLeu--Leu-lle-dThr-20 Gly-Leu-Lys-Gly-NH2 |
| Esc 8 | 9 | Gly-Ile-Phe-Ser-Lys-Leu-Ala-10 Gly-Lys-Lys-Ile-Lys-Asn-dLeu--Leu-Ile-20 Thr-Gly-Leu-Lys-Gly-NH2 |
| Esc 9 | 10 | Gly-Ile-Phe-Ser-Lys-Leu-Ala-10 Gly-Lys-Lys-Ile-Lys-Asn-dLeu--Leu-Ile-dTrp-20 Gly-Leu-Lys-Gly-NH2 |
| Esc 10 | 11 | Gly-Ile-Phe-Ser-Lys-Leu-Ala-10 Gly-Lys-Lys-Ile-Lys-Asn-dLeu-Leu-Ile-Trp-Gly-20 Leu-Lys-Gly-NH2 |

Direct Modulation of Cl Current by Esc AMPs

After 24 h incubation of FRT cells with 1 µM Vx-809, patch-clamp experiments were done to investigate the mechanism of CFTR activation by AMPs. In whole-cell recordings, CFTR was activated by FSK (20 µM) in combination with Esc peptides (10 µM) or the well-known CFTR potentiator GEN (50 µM), all added in the extracellular solution. The data showed that addition of both peptides at the extracellular side of the membrane patch, according to the whole-cell configuration, induced a significant increase of the current intensity, indicating a significant recovery of the mutated channel activity, similarly to the effect associated to 50 µM genistein.

Importantly when the CFTR inhibitor CFTR$_{inh}$-172 (10 µM) was added, the current intensity reverted to the values measured before CFTR activation, meaning that, as already demonstrated for genistein, enhanced peptide-induced Cl–ions current implies activation of CFTR.

CFTR activation was also studied under cell-free conditions by the inside-out patch-clamp configuration using large pipette tips in order to obtain macro-patches containing multiple CFTR channels. After inducing phosphorylation of CFTR by the addition of ATP and the catalytic subunit of PKA, the administration of Esc peptides in the internal bath solution clearly increased CFTR activity, as experienced by the significant enhancement of ion current. Also in this case, the currents activated by AMPs were rapidly blocked by the specific CFTR inhibitor CFTRinh-172 (10 µM), thus supporting the conclusion that Esc peptides are able to potentiate CFTR channel activity by direct binding to it.

The invention claimed is:

1. A method for treating cystic fibrosis in an individual in need thereof who does not have a *P. aeruginosa* infection, the method comprising:
   (a) selecting an individual diagnosed with cystic fibrosis who does not have a *P. aeruginosa* infection;
   (b) providing a pharmaceutical formulation comprising:
      (1) a pharmaceutically active ingredient comprising:
         (i) an esculentin-1a(1-21)$NH_2$ peptide having an amino acid sequence as set forth in SEQ ID NO:2; or
         (ii) an esculentin diastereomer Esc(1-21)-1c having an amino acid sequence as set forth in SEQ ID NO:3; and
      (2) a pharmaceutically acceptable adjuvant, vehicle or excipient, and
   (c) administering the pharmaceutical formulation to the individual who does not have a *P. aeruginosa* infection.

2. The method of claim 1, further comprising administering to the individual in need thereof who does not have a *P. aeruginosa* infection at least one modulator of cystic fibrosis transmembrane conductance regulator (CFTR).

3. The method of claim 1, wherein the cystic fibrosis transmembrane conductance regulator (CFTR) is selected from the group consisting of: Ivacaftor, Lumacaftor, Tezacaftor, VX-445, VX-659, VX-152, VX-440, VX-561 (CTP-656), QBW251, FDL169, GLPG1837, GLPG2222, GLPG2451, GLPG2737, GLPG3067, GLPG3067, PTI-428, PTI-801, PTI-808, QR-010, MRT5005, QBW276, SPX-101, AZD5634, BI 443651, and a mixture thereof.

4. The method of claim 1, wherein the pharmaceutically active ingredient consists of:
   (i) an esculentin-1a(1-21)$NH_2$ peptide having an amino acid sequence as set forth in SEQ ID NO:2; and
   (ii) an esculentin diastereomer Esc(1-21)-1c having an amino acid sequence as set forth in SEQ ID NO:3.

5. The method of claim 1, wherein the pharmaceutically acceptable adjuvant comprises a solubilizing agent, a dispersing agent, a suspension agent, an emulsifying agent or a combination thereof.

6. The method of claim 1, wherein the pharmaceutically active ingredient comprises:
   (a) an esculentin-1a(1-21)$NH_2$ peptide having an amino acid sequence as set forth in SEQ ID NO:2; and
   (b) an esculentin diastereomer Esc(1-21)-1c having an amino acid sequence as set forth in SEQ ID NO:3.

* * * * *